Figure 1:
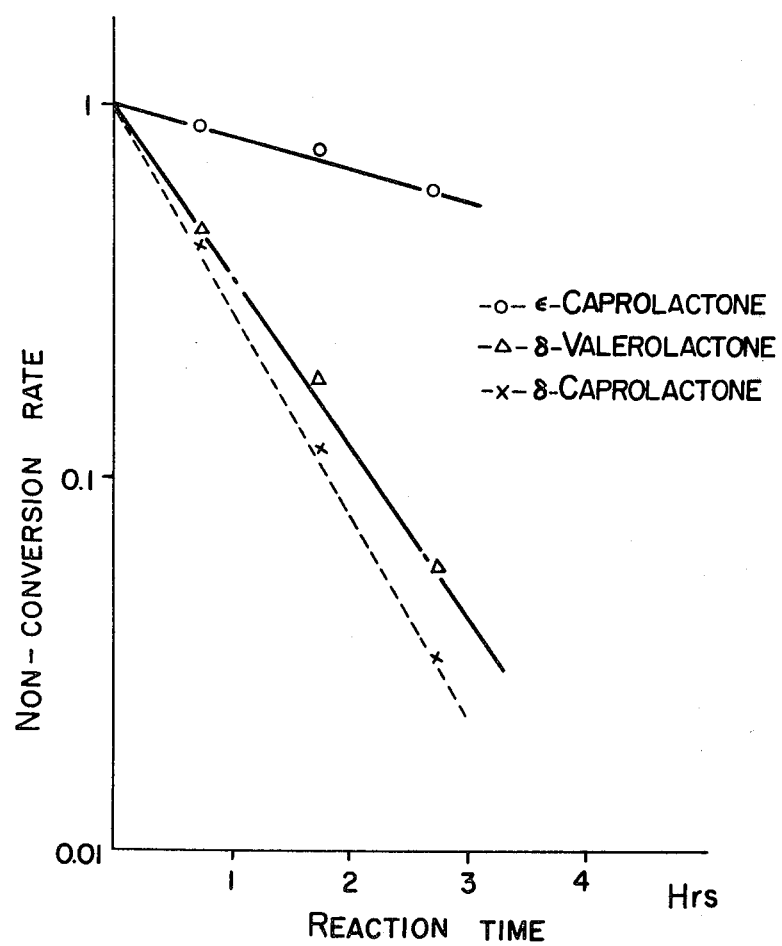

United States Patent [19]

Fujita et al.

[11] 3,953,472

[45] Apr. 27, 1976

[54] METHOD FOR SEPARATING LACTONES FROM A MIXTURE CONTAINING LACTONES

[75] Inventors: Yutaka Fujita; Toru Sawaki; Tadahisa Sasano, all of Iwakuni; Masao Sada, Kobe, all of Japan

[73] Assignees: Teijin Limited; Sumitomo Chemical Company, Limited, both of Osaka, Japan

[22] Filed: Mar. 15, 1974

[21] Appl. No.: 451,564

[30] Foreign Application Priority Data

Mar. 17, 1973 Japan.............................. 48-30510

[52] U.S. Cl............................ 260/343; 260/343.5; 260/343.6; 260/419; 260/484 R; 260/535 R
[51] Int. Cl.²....................................... C07D 307/12
[58] Field of Search............ 260/343.5, 343.6, 343, 260/535, 484, 419

[56] References Cited
UNITED STATES PATENTS

| | | | |
|---|---|---|---|
| 2,234,551 | 3/1941 | Collaud............................... | 260/343 |
| 2,936,310 | 5/1960 | Beets et al. ......................... | 260/343 |
| 3,277,168 | 10/1966 | Koenig................................. | 260/343 |
| 3,624,258 | 11/1971 | Ishimoto et al..................... | 260/343 |
| 3,825,570 | 7/1974 | Fujita et al.......................... | 260/343 |

*Primary Examiner*—James A. Patten
*Attorney, Agent, or Firm*—Stevens, Davis, Miller & Mosher

[57] ABSTRACT

Lactones are separated from a mixture of (a) at least one member selected from the group consisting of hydroxy acids wherein the OH group and the COOH group are bonded through 3 or 4 carbon atoms, lactones derived therefrom, lower polymers of said hydroxy acids and/or said lactones and esters of said hydroxy acids and/or said lactones and (b) at least one member selected from the group consisting of hydroxy acids wherein the OH group and the COOH group are bonded through 5 carbon atoms, lactones derived therefrom, lower polymers of said hydroxy acids and/or said lactones and esters of said hydroxy acids and/or said lactones, by heating said mixture in the presence of one or more monovalent or bivalent aliphatic or alicyclic alcohols under the conditions so as to remove the lactones from said (a) by distillation.

12 Claims, 3 Drawing Figures

METHOD FOR SEPARATING LACTONES FROM A MIXTURE CONTAINING LACTONES

This invention relates to a method for separating lactones from a mixture of (a) at least one member selected from the group consisting of hydroxy acids wherein the OH group and the COOH group are bonded through 3 or 4 carbon atoms, lactones derived therefrom, lower polymers of said hydroxy acids and/or said lactones and esters of said hydroxy acids and/or said lactones, and (b) at least one member selected from the group consisting of hydroxy acids wherein the OH group and the COOH group are bonded through 5 carbon atoms, lactones derived therefrom, lower polymers of said hydroxy acids and/or said lactones and esters of said hydroxy acids and/or said lactones, more particularly to a method for separating lactones by subjecting said mixture of (a) and (b) to the conditions of cyclizing the hydroxy acids in (a) to the corresponding lactones and of removing the lactones in (a) by distillation.

In the present invention, the hydroxy acids wherein the OH group and the COOH group are bonded through 3 carbon atoms, in said (a) include, for example, $\gamma$-hydroxybutyric acid, $\gamma$-hydroxyvaleric acid, $\gamma$-hydroxycaproic acid, $\gamma$-hydroxyenanthoic acid, $\gamma$-hydroxycaprylic acid, and the like, and the lactones corresponding to said hydroxy acids include, for example, $\gamma$-butyrolactone, $\gamma$-valerolactone, $\gamma$-caprolactone, $\gamma$-enantholactone, $\gamma$-caprylolactone, and the like. The hydroxy acids wherein the OH group and the COOH group are bonded through 4 carbon atoms in said (a) include, for example, $\delta$-hydroxyvaleric acid, $\delta$-hydroxycaproic acid, $\delta$-hydroxyenanthoic acid, $\delta$-hydroxycaprylic acid, and the like, and the lactones corresponding to said hydroxy acids include, for example, $\delta$-valerolactone, $\delta$-caprolactone, $\delta$-enantholactone, $\delta$-caprylolactone, and the like. The hydroxy acids wherein the OH group and the COOH group are bonded through 5 carbon atoms in said (b) include, for example, $\epsilon$-hydroxy caproic acid, $\epsilon$-hydroxy enanthoic acid, $\epsilon$-hydroxy caprylic acid, and the like, and the lactones corresponding to said hydroxy acids include, for example, $\epsilon$-caprolactone, $\epsilon$-enantholactone, $\epsilon$-caprylolactone, and the like. Lactones may also include $\gamma$, $\delta$, or $\epsilon$-lactones wherein one or more hydrogen atoms at the $\alpha$, $\beta$, or $\gamma$ position are substituted by one or more alkyl groups.

By the reaction with ammonia, $\epsilon$-caprolactone can easily be converted to $\epsilon$-caprolactam, which is a very important intermediate for preparing nylon 6.

In order to separate $\epsilon$-caprolactone from other lactones, e.g. $\delta$-caprolactone, $\delta$-valerolactone, there has been proposed a separation method by distillation using the differences in relative volatilities between $\epsilon$-caprolactone and other lactones. But relative volatilities between $\epsilon$-caprolactone and other lactones at a pressure of 30 mmHg abs. are as follows:

1.27 between $\delta$-caprolactone and $\epsilon$-caprolactone,
1.42 between $\delta$-valerolactone and $\epsilon$-caprolactone,
1.83 between $\gamma$-caprolactone and $\epsilon$-caprolactone,
3.00 between $\gamma$-valerolactone and $\epsilon$-caprolactone, and
3.45 between $\gamma$-butyrolactone and $\epsilon$-caprolactone.

For example, in order to separate $\epsilon$-caprolactone from $\delta$-valerolactone by distillation, many numbers of plates are necessary and the separation of $\epsilon$-caprolactone from $\delta$-caprolactone by distillation seems to be almost impossible.

On the other hand, lactones including $\epsilon$-caprolactone are unstable for heat and begin to polymerize immediately by heating. Therefore, it is necessary to avoid heating above 150°C for a long time. Further, since many numbers of plates are necessary for the separation by distillation, both the pressure and temperature at the bottom of a tower may increase. In order to avoid such a state, the pressure at the top of a tower has to be kept lower. For example, if a distillation tower having 25 plates is used, and a pressure drop at each plate is assumed to be 2 mmHg, the total pressure drop would be 50 mmHg and the pressure at the top of the tower should be maintained below 5 mmHg in order to maintain the temperature in the tower below 150°C. As mentioned above, the separation of $\epsilon$-caprolactone from other lactones by distillation has various defects and therefore it is very disadvantageous to employ such a method industrially.

In addition, it should be noted that in order to obtain $\epsilon$-caprolactam in high purity by the reaction of $\epsilon$-caprolactone with ammonia it is necessary to use highly pure $\epsilon$-caprolactone.

In the study on the separation of each group from said mixture of (a) and (b) overcoming the defects mentioned above, the present inventors have found that when said mixture is heated in the presence of one or more monovalent or bivalent aliphatic or alicyclic alcohols and subjected to suitable distillation conditions for the lactones corresponding to the components in said (a), due to great differences of reactivities of the lactone precursors in the conversion to lactones, said lactones are distilled first and can easily be separated from said mixture. Thus the remaining lactones corresponding to the components in said (b) can also be separated in high yield and have accomplished the present invention.

It is an object of the present invention to provide a method for separating lactones from a mixture of said (a) and (b) overcoming the defects of the known methods. It is another object of the present invention to provide a method for separating lactones from the mixture of said (a) and (b) industrially. Further objects and advantages of this invention will be apparent to one skilled in the art from the accompanying disclosure and discussion.

The present invention provides a method for separating lactones from a mixture comprising a. at least one member selected from the group consisting of hydroxy acids wherein the OH group and the COOH group are bonded through 3 or 4 carbon atoms, lactones derived therefrom, lower polymers of said hydroxy acids and/or said lactones and esters of said hydroxy acids and/or said lactones, and b. at least one member selected from the group consisting of hydroxy acids wherein the OH group and the COOH group are bonded through 5 carbon atoms, lactones derived therefrom, lower polymers of said hydroxy acids and/or said lactones and esters of said hydroxy acids and/or said lactones, which comprises heating said mixture in the presence of one or more monovalent or bivalent aliphatic or alicyclic alcohols under the conditions so as to remove the lactones derived from the hydroxy acids wherein the OH group and the COOH group are bonded through 3 or 4 carbon atoms by distillation.

In the present invention, as the starting mixture comprising said (a) and (b), any mixtures obtained by any processes can be employed. A mixture comprising oligomers of hydroxy acids containing polymers of ε-hydroxycaproic acid having polymerization degree of about 10 or less may also be employed. Another example of said mixture is a reaction mixture obtained by selectively hydrogenating, in the presence of the alcohol as mentioned below and a reduced cobalt catalyst, a reaction mixture containing ε-hydroxycaproic acid, adipic acid and formylvaleric acid as major components and glutaric acid, 5-oxocaproic acid, etc., which is obtained by oxidizing cyclohexane at 120°–170°C under a pressure of 3 – 20 kg/cm² G by air and successively extracting with water. Said reaction mixture generally contains ε-hydroxycaproic acid and other hydroxy acids as esters of adipic acid and esters of the alcohols as mentioned below and may further contain the unreacted adipic acid and the alcohols as mentioned below and the like. Esters of hydroxy acids including ε-hydroxycaproic acid as mentioned above may also be used as a starting mixture. Esters or lower polymers obtained by heating lactones including ε-caprolactone in the presence or absence of the alcohol as mentioned below may also be used as a starting mixture.

According to the method of the present invention, said starting mixture is heated in the presence of one or more monovalent or bivalent aliphatic or alicyclic alcohols (hereinafter referred to as alcohols) under the conditions so as to remove the lactones derived from the hydroxy acids wherein the OH group and the COOH group are bonded through 3 or 4 carbon atoms by distillation. It is preferable to use said alcohols in an amount of satisfying the following conditions:

$$X - Y \geqq 0.02 Z \quad (1)$$

wherein $X$ is the total number of hydroxyl groups in the reaction system, $Y$ is the total number of carboxyl groups in the reaction system, and $Z$ is the total number of carboxyl groups in the ε-hydroxycaproic acid and the other hydroxy acids, the lower polymers thereof, the lactones corresponding to them, and the esters thereof, provided that an ester bond is calculated as one carboxyl group and one hydroxyl group.

As the alcohols, monovalent aliphatic or alicyclic alcohols having preferably 10 or more carbon atoms, more preferably 10 – 30 carbon atoms, or bivalent aliphatic or alicyclic alcohols having 2 or more carbon atoms, more preferably 2 – 30 carbon atoms are preferable. Examples of the monovalent alcohols are decanol, undecanol, dodecanol, tridecanol, tetradecanol, cyclodecanol, cyclopentadecanol, and the like, and examples of the bivalent alcohols (diols) are ethylene glycol, propylene glycol, butanediol, pentanediol, hexanediol, heptanediol, octanediol, nonanediol, decanediol, undecanediol, dodecanediol, tridecanediol, tetradecanediol, pentadecanediol, octadecanediol, nonadecanediol, and the like. Above all alcohols having higher boiling points than those of the lactones corresponding to the hydroxy acids in said (a) and (b) such as 1-dodecanol, 1,5-pentanediol, 1,6-hexanediol, 1,7-heptanediol, 1,8-octanediol, 1,9-nonanediol, 1,10-decanediol, 1,11-undecanediol and 1,12-dodecanediol are more preferable. When ethylene glycol or propylene glycol, the boiling point of which is lower than those of said lactones, is used, it is added to the reaction system continuously or intermittently to carry out the reaction effectively since it can be removed by distillation from the reaction system relatively fast. Alcohols are used in the reaction system so as to be present in excess of free alcoholic hydroxyl groups.

The starting mixture comprising said (a) and (b) is heated under the conditions so as to remove the lactones corresponding to the hydroxy acids in said (a) by distillation, for example, at a temperature of 180° – 340°C under a pressure of 0.1 – 500 mmHg abs., preferably at a temperature of 200° – 270°C under a pressure of 10 – 400 mmHg abs.

According to the method of the present invention, lactones such as δ-caprolactone and δ-valerolactone corresponding to the hydroxy acids in said (a) are condensed in the distillate much more than in the starting mixture, while in the bottom ε-caprolactone, lower polymers of ε-hydroxycaproic acid, esters of ε-caprolactone and the hydroxy acid, in said (b) are condensed. This can be explained concretely using the accompanying FIG. 1. FIG. 1 shows the relation between the non-conversion rate of hydroxy acids and reaction time in the case of conversion of the hydroxy acids to the corresponding ε-caprolactone, δ-valerolactone and δ-caprolactone to be measured at 260°C under a pressure of 30 mmHg abs.

The reactions of ε-hydroxycaproic acid and other hydroxy acids and/or their precursors to the corresponding lactones are first-order reaction. When a starting mixture is heated in the presence of a monovalent or bivalent aliphatic or alicyclic alcohol at 260°C under a pressure of 30 mmHg abs., the ratio of rate constants in the reactions of hydroxy acids other than ε-hydroxycaproic acid to the corresponding lactones to that in the reaction of ε-hydroxycaproic acid to ε-caprolactone is 6.44 in the case of δ-caprolactone and 5.30 in the case of δ-valerolactone. Said rate constant ratios show easiness in the separation of ε-caprolactone from other lactones. The greater values of both relative volatility and rate constant ratio which corresponds to relative volatility in distillation become, the easier a separation operation is. The relative volatilities of δ-caprolactone and δ-valerolactone to ε-caprolactone are as small as 1.27 and 1.42 as mentioned above. Presuming the separation of an admixed solution the composition of which is ε-caprolactone 0.90, δ-caprolactone 0.03 and δ-valerolactone 0.07 in mole fraction up to the solution having the composition of ε-caprolactone 0.97, δ-caprolactone 0.01 and δ-valerolactone 0.02 with a 2 % loss, the minimum number of theoretical plates calculated by using the Fenske equation is 19 in the case of the relative volatility being 1.27, 1.5 in the case of the relative volatility being 6.44, and 13.3 in the case of the relative volatility being 1.42, and 2 in the case of the relative volatility being 5.30. These results apparently show the superioity of the separating method of the present invention comparing with the known method.

Figure 2:
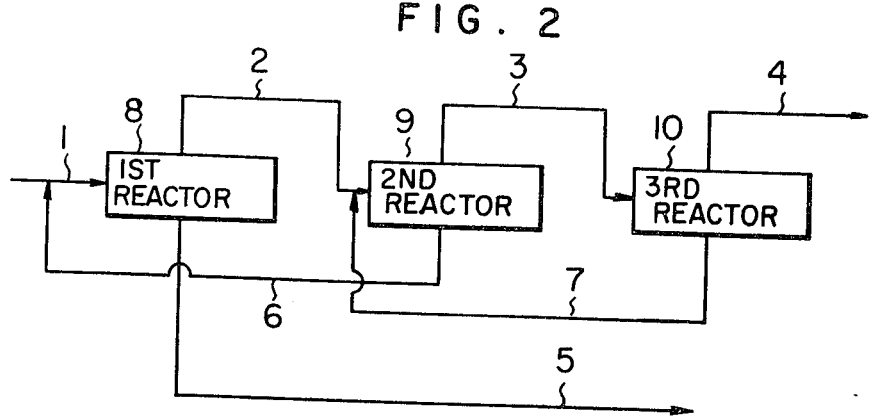

FIG. 2 is a flow sheet suitable for carrying out the method of the present invention. In FIG. 2, a starting mixture is fed to 1st reactor 8 through line 1. The starting mixture for 1st step is reacted in 1st reactor until the desired degree of separation is obtained. Bottoms from 1st reactor having the desired purity are taken off through line 5 as a product. Distillate from 1st reactor containing a considerable amount of ε-caprolactone and being short of the desired yield is heated and fed to 2nd reactor 9 through line 2 as the starting mixture for 2nd step. In 2nd reactor, distillate from 1st reactor is condensed so as to have the same concentrations of ε-caprolactone and its precursor derivatives as those of the starting mixture for 1st reactor. Bottoms from 2nd reactor is recycled to 1st reactor through line 6. Distillate from 2nd reactor is fed to 3rd reactor 10 through line 3 in order to increase further the yield. In 3rd reactor, ε-caprolactone and its precursor derivatives in distillate from 2nd reactor are condensed to the same concentrations as those of the starting mixture for 2nd reactor. Bottoms from 3rd reactor are recycled to 2nd reactor through line 7. Distillate from 3rd reactor is taken off through line 4. The thus obtained distillate from 3rd reactor contains a small amount of ε-caprolactone. If the loss of ε-caprolactone is small enough to meet the desired yield, the separation procedures are to be completed. If the desired yield can not be attained at the completion of the reaction in 3rd reactor, distillate from 3rd reactor is fed to 4th reactor wherein a reaction similar to that of 3rd reactor is carried out to obtain the desired result.

As clear from the flow sheet of FIG. 2, number of reactors has the same meaning as that of plates in distillation. Therefore, by repeating a procedure of using distilled lactones containing ε-caprolactone as a starting material for the next reactor as mentioned above, operation of enriching section in distillaton is possible. Further, by using bottoms containing ε-caprolactone and/or its precursors and other lactones and/or their precursors as a starting material again as mentioned above, operation of recovering section in distillation is possible.

Figure 3:
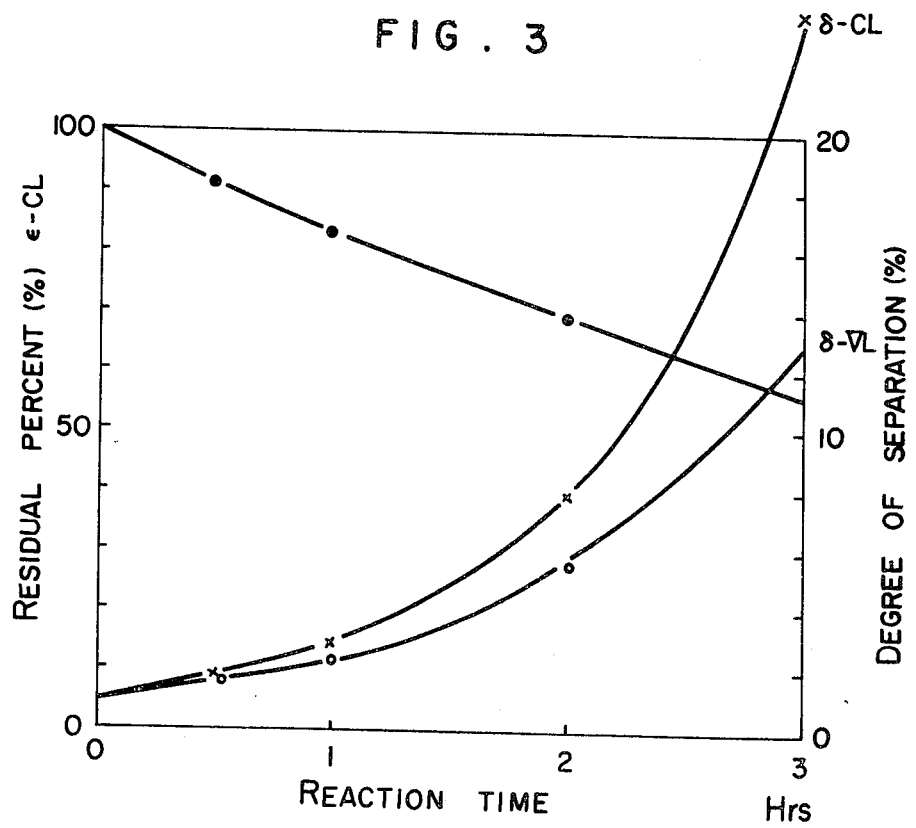

FIG. 3 shows the relation between effect on separation and yield in the method of the present invention. In FIG. 3, residual percent of ε-caprolactone (ε-CL) which shows yield is plotted as ordinate (the left-hand axis) and degree of separation of δ-caprolactone (δ-CL) and δ-valerolactone (δ-VL) is plotted as ordinate (the right-hand axis) and reaction time is plotted as abscissa. It is found that reflux ratio in distillation can be shown by the ratio of residual percent to conversion. Since the reactions of ε-hydroxycaproic acid to ε-caprolactone and other hydroxy acids to the corresponding lactones are first-order, the ratio of residual percent of the reactant to conversion can be expressed by the product of rate constant and reaction time. Therefore, under definite reaction conditions, reaction time is a factor for determining reflux ratio in distillation. Accordingly the most preferable reaction time can be determined by a combination of reaction temperature and pressure together with the desired degree of separation and yield.

As mentioned above, since the bottoms after the separation of other lactones and their precursor derivatives contain mainly ε-caprolactone and its precursor derivatives, highly pure ε-caprolactone can easily be obtained by using said bottoms as a starting material in a evaporating process, for example, disclosed in Japanese Patent Publication Sho 47-15956 (15956/1972).

Further, according to the method of the present invention, if materials having lower boiling points than those of lactones, for example, cyclohexanol, n-pentanol, n-hexanol, cyclopentanone, caproic acid, valeric acid and its esters, etc. are included, the separation of these materials from ε-caprolactone and its precursor is also possible since these materials are heated in the presence of an excess amount of the compound having alcoholic hydroxyl group or groups as mentioned above and are substituted by said alcohols to be distilled off and removed.

As an apparatus for carrying out the reaction and separation according to the method of the present invention, any ones which have sections for heating under reduced pressure the starting mixture under the conditions mentioned above, evaporating and collecting lactones in the reaction section may be used. It is preferable to use a reaction apparatus equipped with a rectifying section or a cooling section so as to recycle the vapors of the starting mixture and reaction intermediates except for lactones including ε-caprolactone to the reaction vessel in order to separate lactones in high yield. As the rectifying section, those industrially widely used as rectifying columns such as a packed rectification column, a perforated plate column, a bubble cap column, and the like may be used.

As the reactor which can heat a starting mixture and evaporate the produced lactones including ε-caprolactone, those industrially widely used as evaporators such as a natural convection evaporator, a forced circulation evaporator, a thin layer evaporator, and the like may be used. Further evaporators of any types which have a volume necessary for retaining a starting mixture for the period necessary for separation and a heat transferring area necessary for heating a starting mixture under reduced pressure and for evaporating the produced lactones including ε-caprolactone may be used as a reactor in the method of the present invention.

The distillate obtained as mentioned above includes δ- and γ- lactones and in some cases a small amount of ε-caprolactone and alcohols added to the reaction system, dimers of ε-caprolactone and other lactones, esters of ε-hydroxycaproic acid and other hydroxy acids with said alcohols, but it does not include ε-hydroxycaproic acid and other hydroxy acids. It is also possible to separate lactones including a small amount of ε-caprolactone from said alcohols, said dimers and said esters by distillation and to recycle said alcohols and/or said dimers and said esters to the reaction system.

It is not necessary to add a catalyst to the reaction system in carrying out the method of the present invention, but a compound known as an ester interchange catalyst such as orthoboric acid, magnesium oxide, zinc oxide, sodium hydroxide, magnesium chloride or the like may be added to the reaction system.

The invention is illustrated more particularly by way of the following examples.

EXAMPLE 1

Fourty-five g of ε-caprolactone, 10 g of δ-valerolactone, 5 g of δ-caprolactone and 40 g of 1,6-hexanediol were mixed at room temperature and then the resulting mixture was heated for 5 hours at 100°C to produce the reaction mixture containing hydroxy acid esters and lower polymer derived therefrom. A 250 cc round bottomed glass flask surrounded by heating belt consisting of asbestos cloth and nichrome wire and equipped at the top of it with a packed rectification glass column having an internal diameter of 1.5 cm and filled with ¼inch Dickson packing in 100 cm length was used. In the flask, 100 g of said reaction mixture was placed and heated at 220°C for 4 hours under a pressure of 100 mmHg abs. with the reflux ratio of 0.5. There were obtained 35.5 g of distillate product containing 9 g of ε-caprolactone, 7 g of δ-valerolactone, 4.5 g of δ-caprolactone and 15 g of 1,6-hexanediol, and 64 g of the bottom product containing 36 g of ε-caprolactone and ε-hydroxy caproic acid, their lower polymers and their esters converted to a ε-caprolactone basis, 2.7 g of δ-valerolactone and δ-hydroxyvaleric acid, their lower polymers and their esters converted to a δ-valerolactone basis, and 0.4 g of δ-caprolactone and δ-hydroxycaproic acid, their lower polymers and their esters converted to a δ-caprolactone basis.

The conversion to δ-valerolactone was 70 % and the conversion of δ-caprolactone was 95 %. The loss of ε-caprolactone was 20 %. The concentrations of lactones in the bottom product converted to each lactone basis were 92.1 % by weight of ε-caprolactone, 6.9 % by weight of δ-valerolactone and 1.0 % by weight of δ-caprolactone.

EXAMPLE 2

Forty-five g of δ-caprolactone, 10 g of δ-valerolactone, 5 g of δ-caprolactone and 40 g of various alcohols as listed in Table 1 were mixed and then the resulting mixture was heated at 100°C for 5 hours to produce the reaction mixture containing hydroxy acids and lower polymers derived therefrom. In the flask used in Example 1, 100 g of said reaction mixture was placed and heated at 250°C for 4 hours under a pressure of 30 mmHg abs. with the reflux ratio of 0.5.

The results are shown in Table 1.

Table 1

| Alcohol | Conversion (%) δ-Valero-lactone | δ-Capro-lactone | Loss (%) ε-Capro-lactone | Composition of the bottoms(%)* δ-Valero-lactone | δ-Capro-lactone | ε-Capro-lactone |
|---|---|---|---|---|---|---|
| 1-Dodecanol | 85 | 92 | 23 | 4.1 | 1.0 | 94.9 |
| 1,5-Pentanediol | 88 | 94 | 18 | 3.1 | 0.8 | 96.1 |
| 1,8-Octanediol | 86 | 89 | 15 | 3.5 | 1.4 | 95.1 |
| 1,10-Decanediol | 90 | 86 | 21 | 2.7 | 1.8 | 95.5 |
| 1,6-Hexanediol | 89 | 97 | 20 | 2.9 | 0.4 | 96.7 |

Note: *Composition of the bottoms is expressed by percent by weight converted to each lactone basis.

EXAMPLE 3

Cyclohexane and cyclohexanone were oxidized by air at 140°C under a pressure of 6 kg/cm² G and the obtained products were extracted with water. To the extract, 1,6-hexanediol was added double the equivalent of the free carboxylic acids in the extract and the resulting mixture was hydrogenated at 210°C under a pressure of hydrogen at 50 kg/cm² G in the presence of a cobalt catalyst prepared by sintering at 1500°C followed by reduction. Then the water was removed by a simple distillation at 100°C under a reduced pressure of 50 mmHg abs. The thus obtained mixture was used as a starting mixture which contained ε-caprolactone and ε-hydroxycaproic acid, their lower polymers and their esters in 16.24% by weight converted to a ε-caprolactone basis, δ-caprolactone and δ-hydroxycaproic acid, their lower polymers and their esters in 0.52 % by weight converted to a δ-caprolactone basis, δ-valerolactone and δ-hydroxyvaleric acid, their lower polymers and their esters in 0.95 % by weight converted to a δ-valerolactone basis, 61.77 % by weight of 1,6-hexanediol and 9.79 % by weight of adipic acid. When the composition mentioned above is expressed based on only lactones including ε-caprolactone, the starting mixture contained 91.00 mole % of ε-caprolactone, 2.94 mole % of δ-caprolactone and 6.06 mole % of δ-valerolactone.

In the flask used in Example 1, 60 g of said starting mixture was placed and heated at 220°C for 4 hours under a pressure of 100 mmHg abs. with the reflux ratio of 0.5. There were obtained 18.3 g of the distillate product containing 1.11 g of ε-caprolactone, 0.31 g of δ-caprolactone, 0.34 g of δ-valerolactone, and 11.59 g of 1,6-hexanediol, and 40.8 g of the bottom product containing 8.44 g of ε-caprolactone, 0.002 g of ε-caprolactone, 0.23 g of δ-valerolactone (these values being converted ones as mentioned above), 5.87 g of adipic acid and 24.3 g of 1,6-hexanediol.

The conversion to δ-caprolactone was 99.3 % and the conversion to δ-valerolactone was 59.6 %. The loss of ε-caprolactone was 11.4 %. The concentrations of lactones in the bottom product converted to each lactone basis were 96.96 mole % of ε-caprolactone, 0.03 mole % of δ-caprolactone and 3.01 mole % of δ-valerolactone.

EXAMPLE 4

Cyclohexane and cyclohexanone were oxidized by air at 140°C under a pressure of 6 kg/cm² G and the obtained products were extracted with water. To the extract, 1,12-dodecanediol was added double the equivalent of the free carboxylic acids in the extract and the resulting mixture was hydrogenated at 210°C under a pressure of hydrogen at 50 kg/cm² G in the presence of a cobalt catalyst prepared by sintering at 1500°C followed by reduction. Then the water was removed by a simple distillation at 100°C under a reduced pressure of 50 mmHg abs. The thus obtained mixture was used as a starting mixture which contained ε-caprolactone and ε-hydroxycaproic acid, their lower polymers and their esters in 11.69 % by weight converted to a ε-caprolactone basis, δ-caprolactone and δ-hydroxycaproic acid, their lower polymers and their esters in 0.40 % by weight converted to a δ-caprolactone basis, 67 -valerolactone and δ-hydroxyvaleric acid, their lower polymers and their esters in 0.78 % by weight converted to a δ-valerolactone basis, 76.09 % by weight of 1,12-dodecanediol and 7.04% by weight of adipic acid. When the composition mentioned above is expressed based on only lactones including ε-caprolactone, the starting mixture contained 90.1 mole % of ε-caprolactone, 3.1 mole % of δ-caprolactone and 6.8 mole % of δ-valerolactone.

In the flask used in Example 1, 120 g of said starting mixture was placed and heated at 260°C for 4 hours under a pressure of 300 mmHg abs. with the reflux ratio of 0.5. There were obtained 4.75 g of the distillate product containing 0.52 g of ε-caprolactone, 0.36 g of δ-caprolactone and 0.76 g of δ-valerolactone, and 114.05 g of the bottom product containing 13.37 g of ε-caprolactone, 0.13 g of δ-caprolactone, 0.18 g of δ-valerolactone (these values being converted ones as mentioned above), 8.45 g of adipic acid and 90.39 g of 1,12-dodecanediol.

The conversion to δ-caprolactone was 73.96 % and the conversion to δ-valerolactone was 80.66 %. The loss of ε-caprolactone was 3.73 %. The concentrations of lactones in the bottom product converted to each lactone basis were 97.58 mole % of ε-caprolactone, 0.92 mole % of δ-caprolactone and 1.50 mole % of δ-valerolactone.

EXAMPLE 5

Cyclohexane and cyclohexanone were oxidized by air at 140°C under a pressure of 6 kg/cm² G and the obtained products were extracted with water. To the extract, 1,6-hexanediol was added double the equivalent of the free carboxylic acids in the extract and the resulting mixture was hydrogenated at 210°C under a pressure of hydrogen at 50 kg/cm² G in the presence of a cobalt catalyst prepared by sintering at 1500°C followed by reduction. Then the water was removed by a simple distillation at 100°C under a pressure of 50 mmHg abs. and further the resulting mixture was simple distilled at 150°C under a pressure of 3 mmHg abs. until the one-third by weight of the charged materials were distilled off. The thus obtained mixture was used as a starting mixture which contained ε-caprolactone and ε-hydroxycaproic acid, their lower polymers and their esters in 24.93 % by weight converted to a ε-caprolactone basis, δ-caprolactone and δ-hydroxycaproic acid, their lower polymers and their esters in 0.83 % by weight converted to a δ-caprolactone basis, δ-valerolactone and δ-hydroxyvaleric acid, their lower polymers and their esters in 1.70 % by weight converted to a δ-valerolactone basis, 47.7 % by weight of 1,6-hexanediol, 15.09 % by weight of adipic acid, as materials having lower boiling points, 1.53 % by weight of cyclohexanol, 0.28 % by weight of n-pentanol and n-hexanol. When the composition mentioned above is expressed based on only lactones including ε-caprolactone, the starting mixture contained 90 mole % of ε-caprolactone, 3 mole % of δ-caprolactone and 7 mole % of δ-valerolactone.

Using an apparatus disclosed in FIG. 2, 400 g of said starting mixture was reacted and separated into lactones and their precursor derivatives. Reaction conditions and reaction time in each reactor were same and as follows: temperature being 260°C, pressure being 30 mmHg abs., reflux ratio being 1 and reaction time being 1.5 hours. As each reactor, a 250 cc round bottomed glass flask surrounded by a heating belt consisting of asbestos cloth and nichrome wire and equipped at the top of it with a packed rectification glass column having an internal diameter of 1.5 cm and filled with ¼ inch Dickson packing in 100 cm length was used. The bottom from 1st reactor was obtained as products. The concentrations of lactones in said bottom product converted to each lactone basis were 97.3 mole % of ε-caprolactone, 0.6 mole % of δ-caprolactone and 2.1 mole % of δ-valerolactone. The loss of ε-caprolactone was 2.5 %. Table 2 shows the material balance at each reactor according to FIG. 2.

Table 2

(Unit:g)

| | | Starting mixture | 1st reactor | 2nd reactor | 3rd reactor |
|---|---|---|---|---|---|
| Composition of starting mixture | ε-CL | (1) 99.52 | 129.49 | 39.95 | 9.99 |
| | δ-CL | 3.32 | 3.93 | 3.80 | 3.20 |
| | δ-VL | 6.80 | 8.50 | 8.13 | 6.42 |
| | AA | 60.36 | 60.36 | — | — |
| | HDO | 190.96 | 224.59 | 82.40 | 48.77 |
| | LBPM | 7.24 | 7.31 | 7.31 | 7.24 |
| | Total | 368.41 | 434.18 | 141.59 | 75.62 |
| Composition of distillate | ε-CL | | (2) 32.27 | (3) 9.99 | (4) 2.50 |
| | δ-CL | | 3.30 | 3.20 | 2.69 |
| | δ-VL | | 6.72 | 6.42 | 5.07 |
| | AA | | — | — | — |
| | HDO | | 72.49 | 48.77 | 38.86 |
| | LBPM | | 7.24 | 7.24 | 7.17 |
| | Total | | 122.12 | 75.62 | 56.29 |
| Composition of bottom | ε-CL | | (5) 97.12 | (6) 29.97 | (7) 7.49 |
| | δ-CL | | 0.63 | 0.61 | 0.51 |
| | δ-VL | | 1.78 | 1.71 | 1.35 |
| | AA | | 60.36 | — | — |
| | HDO | | 152.10 | 33.63 | 9.91 |
| | LBPM | | 0.07 | 0.07 | 0.07 |
| | Total | | 312.06 | 65.99 | 19.33 |

Note:  ε-CL: ε-caprolactone
δ-CL: δ-caprolactone
δ-VL: δ-valerolactone
AA: adipic acid
HDO: 1,6-hexanediol
LBPM: materials having lower boiling points
Numbers (1) through (7) correspond to those in FIG. 2.

What is claimed is:

1. A method for separating lactones from a mixture comprising (a) at least one member selected from the group consisting of saturated aliphatic hydroxy acids wherein the OH group and the COOH group are bonded through 3 or 4 carbon atoms, lactones derived therefrom, lower polymers of said hydroxy acids and/or said lactones and esters of said hydroxy acids and/or said lactones, and (b) at least one member selected from the group consisting of saturated aliphatic hydroxy acids wherein the OH group and the COOH group are bonded through 5 carbon atoms, lactones derived therefrom, lower polymers of said hydroxy acids and/or said lactones and esters of said hydroxy acids and/or said lactones, which comprises treating said mixture in the presence of one or more saturated monovalent or bivalent aliphatic or alicyclic alcohols under a pressure of from 0.1 to 500 mm Hg absolute at a temperature of from 180° to 340°C to remove the lactones derived from the saturated aliphatic hydroxy acids wherein the OH group and the COOH group are bonded through 3 or 4 carbon atoms by distillation.

2. A method according to claim 1, wherein the mixture is one obtained by oxidizing cyclohexane with or without cyclohexanone followed by selective hydrogenation.

3. A method according to claim 1, wherein the mixture is oligomers of hydroxy acids containing polymers of ε-hydroxycaproic acid having the polymerization degree of about 10 or less.

4. A method according to claim 1, wherein the mixture is esters of hydroxy acids including ε-hydroxycaproic acid.

5. A method according to claim 1, wherein the mixture is esters or polymers obtained by heating lactones including ε-caprolactone in the presence or absence of the alcohol defined in claim 1.

6. A method according to claim 1, wherein the alcohol is monovalent aliphatic or alicyclic alcohol having 10 or more carbon atoms.

7. A method according to claim 6, wherein the monovalent aliphatic alcohol is 1-dodecanol.

8. A method according to claim 1, wherein the alcohol is bivalent aliphatic or alicyclic alcohol having 2 or more carbon atoms.

9. A method according to claim 8, wherein the bivalent aliphatic alcohol is 1,5-pentanediol, 1,6-hexanediol, 1,7-heptanediol, 1,8-octanediol, 1,9-nonanediol, 1,10-decanediol, 1,11-undecanediol or 1,12-dodecanediol.

10. A method according to claim 1, wherein one or more reactors equipped with a heating apparatus and a rectifying column are used.

11. A method for separating lactones from a mixture of (a) and (b) defined in claim 1 using two or more reactors which comprises heating said mixture in the presence of one or more monovalent or bivalent aliphatic or alicyclic alcohols under the conditions so as to remove the lactones derived from the hydroxy acids wherein the OH group and the COOH group are bonded through 3 or 4 carbon atoms by distillation in a first reactor, taking off the bottom from the first reactor as a product, feeding the distillate from the first reactor to a second reactor, heating said distillate in the second reactor under the same conditions as applied to the first reactor, recycling the bottom from the second reactor to the first reactor, feeding the distillate from the second reactor to the next reactor, thus repeating heating the distillate from the previous reactor under the same conditions as applied to the first reactor and feeding the distillate to the next reactor while recycling the bottom to the previous reactor.

12. A method according to claim 1, wherein the mixture is one obtained by oxidizing cyclohexane with or without cyclohexanone.

* * * * *